(12) United States Patent
Tsujikawa

(10) Patent No.: US 10,321,027 B2
(45) Date of Patent: Jun. 11, 2019

(54) IMAGING APPARATUS

(71) Applicant: FUJITSU FRONTECH LIMITED, Tokyo (JP)

(72) Inventor: Akinori Tsujikawa, Inagi (JP)

(73) Assignee: Fujitsu Frontech Limited, Tokyo (JP)

( * ) Notice: Subject to any disclaimer, the term of this patent is extended or adjusted under 35 U.S.C. 154(b) by 515 days.

(21) Appl. No.: 14/921,018

(22) Filed: Oct. 23, 2015

(65) Prior Publication Data

US 2016/0044214 A1 Feb. 11, 2016

Related U.S. Application Data

(63) Continuation of application No. PCT/JP2013/064357, filed on May 23, 2013.

(51) Int. Cl.
| | |
|---|---|
| *H04N 5/225* | (2006.01) |
| *G06K 9/00* | (2006.01) |
| *A61B 5/1171* | (2016.01) |
| *A61B 5/117* | (2016.01) |
| *H05K 7/14* | (2006.01) |

(52) U.S. Cl.
CPC ........... *H04N 5/2252* (2013.01); *A61B 5/117* (2013.01); *A61B 5/1171* (2016.02); *H05K 7/1404* (2013.01); *G06K 9/00013* (2013.01)

(58) Field of Classification Search
CPC combination set(s) only.
See application file for complete search history.

(56) References Cited

U.S. PATENT DOCUMENTS

| | | | |
|---|---|---|---|
| 2001/0022882 A1 | 9/2001 | Iwai et al. | |
| 2005/0082081 A1* | 4/2005 | Marcou | H02G 3/088 174/67 |
| 2006/0034499 A1* | 2/2006 | Shinoda | G06K 9/00013 382/124 |
| 2009/0079895 A1* | 3/2009 | Kobayashi | H04M 1/0214 349/58 |

FOREIGN PATENT DOCUMENTS

| | | |
|---|---|---|
| JP | 2534827 Y2 | 5/1997 |
| JP | 2001-256487 | 9/2001 |
| JP | 2011-039275 | 2/2011 |

OTHER PUBLICATIONS

Int'l. Search Report issued in Int'l. App. No. PCT/JP2013/064357, dated Jun. 18, 2013.

* cited by examiner

*Primary Examiner* — Mohammed S Rahaman
*Assistant Examiner* — Samuel D Fereja
(74) *Attorney, Agent, or Firm* — Greer Burns & Crain, Ltd.

(57) ABSTRACT

An image apparatus includes an imaging unit, a housing that houses the imaging unit, a wiring substrate, and a stopper that sandwiches the wiring substrate between the housing and the stopper. The housing has a protruding part that protrudes from a back surface of a side opposite to a front surface on the side of the imaging unit in the wiring substrate. The stopper has an engagement part that engages with an outer peripheral surface of the housing, and a hook part that is hooked onto an inner peripheral surface of the protruding part of the housing.

6 Claims, 12 Drawing Sheets

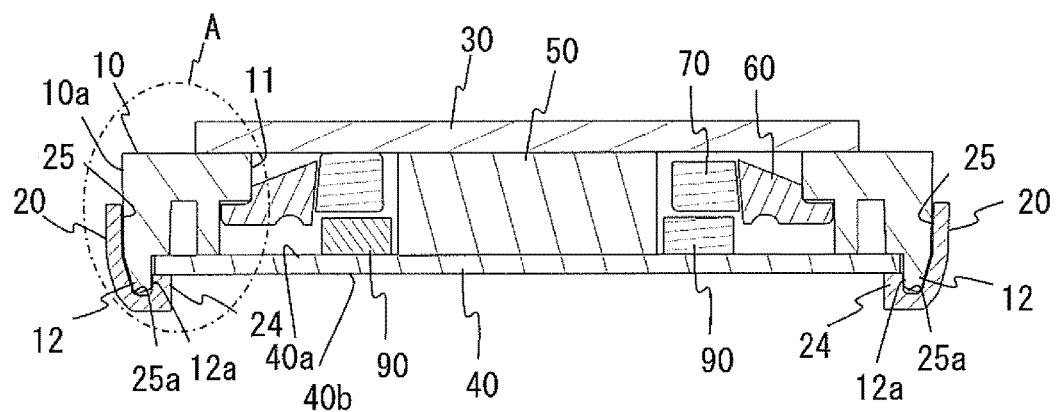
F I G. 4

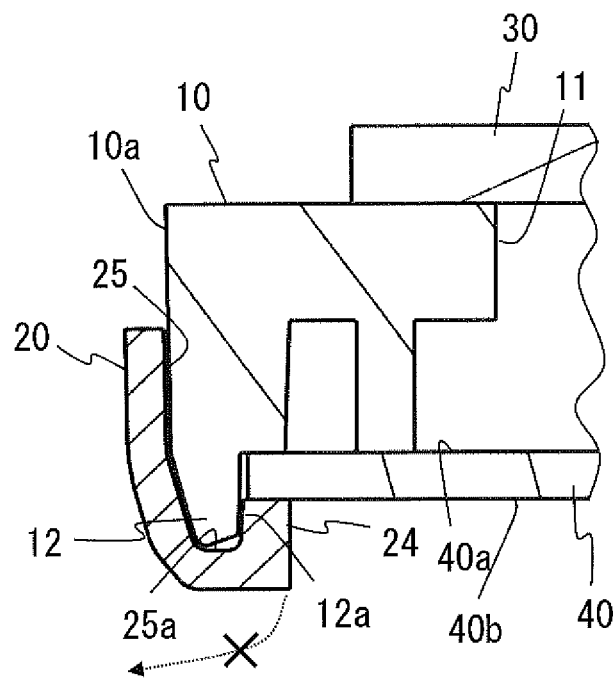
F I G. 7

IMAGING APPARATUS

CROSS-REFERENCE TO RELATED APPLICATION

This application is continuation application of International Application PCT/JP2013/064357 filed on May 23, 2013 and designated the U.S., the entire contents of which are incorporated herein by reference.

FIELD OF THE INVENTION

The present invention relates to an imaging apparatus having stopper that fixes a wiring substrate to a housing.

BACKGROUND OF THE INVENTION

Conventionally, biometric authentication apparatuses that perform authentication by imaging biological information such as veins of the palm, or the like are known.

For a fingerprint matching device, one of such biometric authentication apparatuses, a configuration where a cover is attached to a case by engaging an engagement portion of the cover with that of the case is known (for example, see Japanese Laid-open Patent Publication No. 2001-256487).

As the configuration of the engagement portion, a stopper that is used for a wiring process structure of a washing machine and that sandwiches a substrate between a unit case and the stopper is known (for example, see Utility Model Registration No. 2534827).

BRIEF SUMMARY OF THE INVENTION

The disclosed imaging apparatus includes an imaging unit, a housing that houses the imaging unit, a wiring substrate, and a stopper that sandwiches the wiring substrate between the housing and the stopper. The housing has a protruding part that protrudes from a back surface on a side opposite to a front surface on the side of the imaging unit in the wiring substrate. The stopper has an engagement part that engages with an outer peripheral surface of the housing, and a hook part hooked onto an inner peripheral surface of the protruding part of the housing.

BRIEF DESCRIPTION OF THE SEVERAL VIEWS OF THE DRAWING

FIG. 4 is a IV-IV cross-sectional view of FIG. 1;

FIG. 7 is an enlarged view of a part A of FIG. 4;

DETAILED DESCRIPTION OF THE INVENTION

Figure 9:
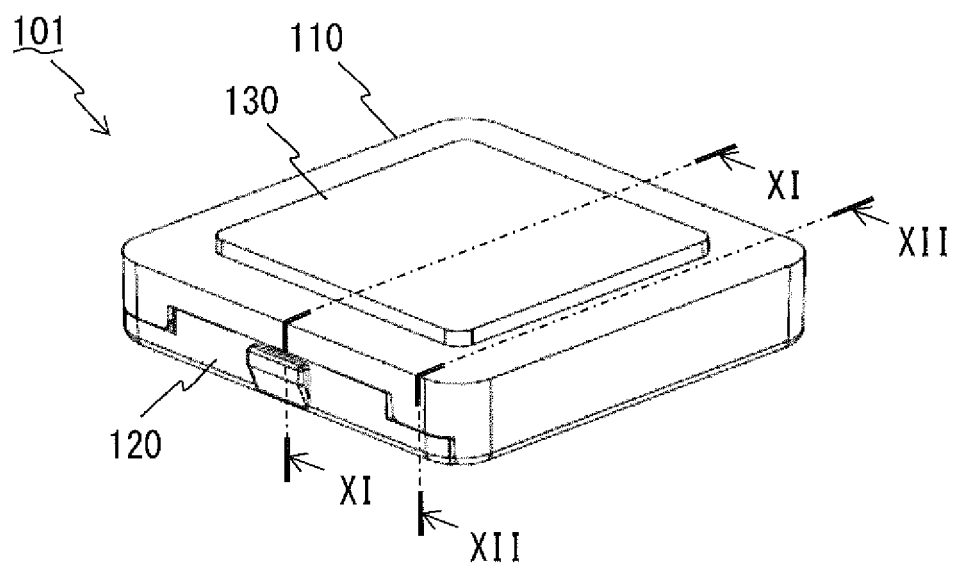
FIG. 9 is a top side perspective view illustrating an imaging apparatus according to a reference technique.

FIG. 9 is a top side perspective view illustrating an imaging apparatus 101 according to a reference technique.

Figure 10:
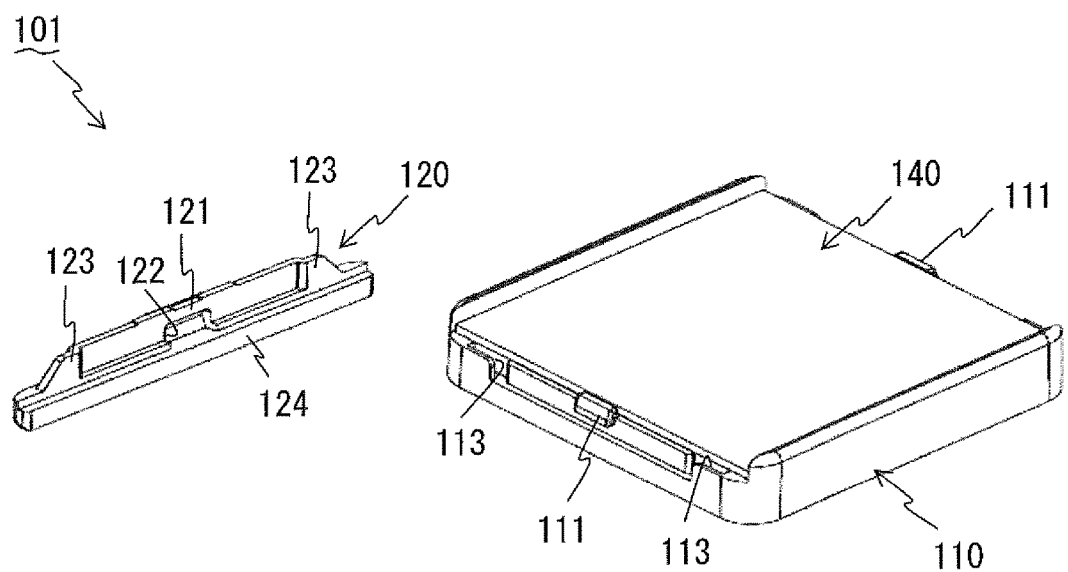
FIG. 10 is a bottom side perspective view illustrating the imaging apparatus, from which a stopper is removed, according to the reference art.

FIG. 10 is a bottom side perspective view illustrating the imaging apparatus 101, from which a stopper 120 is removed, according to the reference technique.

Figure 11:
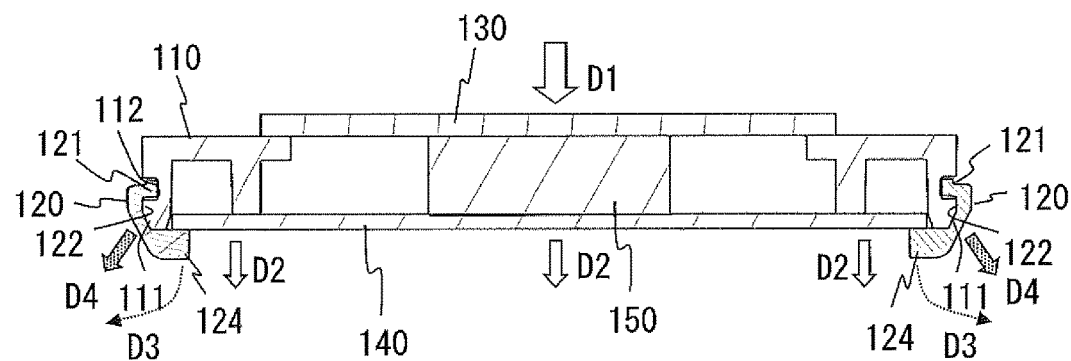
FIG. 11 is an XI-XI cross-sectional view of FIG. 9.
Figure 12:
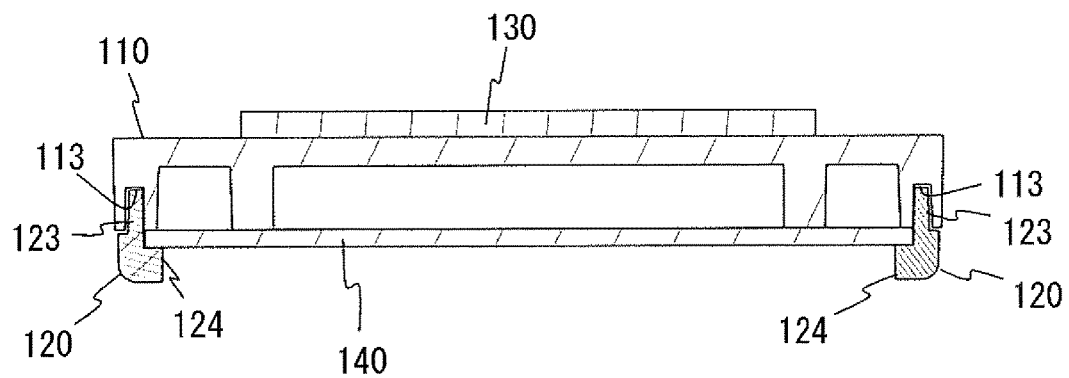
FIG. 12 is a XII-XII cross-sectional view of FIG. 9.

FIGS. 11 and 12 are an XI-XI cross-sectional view and an XII-XII cross-sectional view of FIG. 9.

The imaging apparatus 101 includes a housing 110, two stoppers 120, a top cover 130, a wiring substrate 140, and an imaging unit 150. The imaging apparatus 101 is, for example, a biometric authentication apparatus that images biological information such as veins of the palm, or the like.

The housing 110 takes the shape of a square frame in a planar view. On a top surface of the housing 110, the top cover 130 is arranged. The housing 110 houses the imaging unit 150. The imaging unit 150 includes a lens module not illustrated, and an imaging element, not illustrated, that is mounted on the wiring substrate 140.

The stoppers 120 fix the wiring substrate 140 to the housing 110 by sandwiching the wiring substrate 140 between the housing 110 and the stoppers. The stoppers 120 are respectively arranged on two mutually facing surfaces among four front, back, right and left surfaces, which are an outer peripheral surface of the housing 110. The stoppers 120 configure part of the bottom side on the above described two surfaces. The stoppers 120 are inserted from the bottom side of the housing 110.

The housing 110 includes housing claw parts 111, stopper claw part concave parts 112, and insertion part housing parts 113.

Each of the stoppers 120 has a stopper claw part 121, a housing claw part concave part 122, insertion parts 123, and a substrate pressing part 124.

As illustrated in FIGS. 10 and 11, the housing claw parts 111 are inserted into the housing claw part concave parts 122. On the top of the stopper claw part 121, the housing claw part concave part 122 is formed. Therefore, the stopper claw part 121 protrudes from the housing claw part concave part 122, so that it functions as a claw part. The stopper claw part 121 engages with an outer peripheral surface of the housing 110 by being inserted into the stopper claw part concave part 112 formed on the outer peripheral surface of the housing 110.

As illustrated in FIGS. 10 and 12, the insertion parts 123 are provided on both sides that interpose the stopper claw part 121, and are inserted into the insertion part housing parts 113 that are open on the bottom side.

The substrate pressing parts 124 sandwich the wiring substrate 140 between the housing 110 and the substrate pressing parts 124 by pressing a rim of the bottom surface (back surface) of the wiring substrate 140.

When a load is applied to the top cover 130 downward as illustrated in FIG. 11 (arrow D1) in a case where a target object to be imaged (such as the palm) touches the top cover 130, the force is applied to the wiring substrate 140 (arrow D2). At this time, the insertion parts 123 illustrated in FIGS. 10 and 12 are merely inserted into the insertion part housing parts 113. In contrast, the stopper claw parts 121 illustrated in FIGS. 10 and 11 are inserted into and engage with the stopper claw part concave parts 112. However, force is applied to the stoppers 120 in a direction where the substrate pressing parts 124 separate from the wiring substrate 140 by using the stopper claw part 121 as a pivot point. Thus, the stoppers 120 deviate from the positions at which they sandwich the wiring substrate 140 between the housing 110 and the stoppers 120 (arrow D4).

An imaging apparatus 1 according to an embodiment is described below with reference to the drawings.

Figure 1:
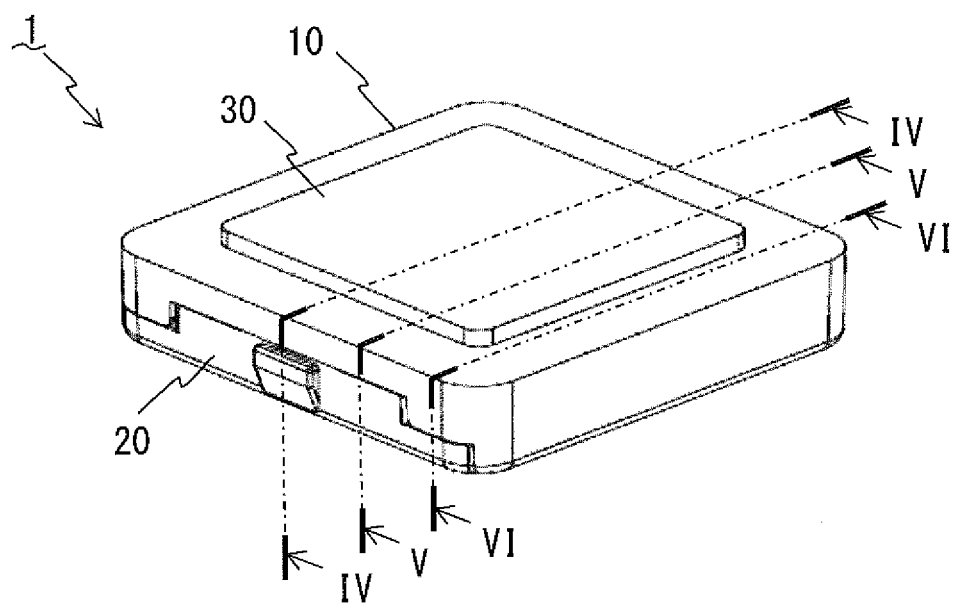
FIG. 1 is a top side perspective view illustrating an imaging apparatus according to an embodiment.
Figure 2:
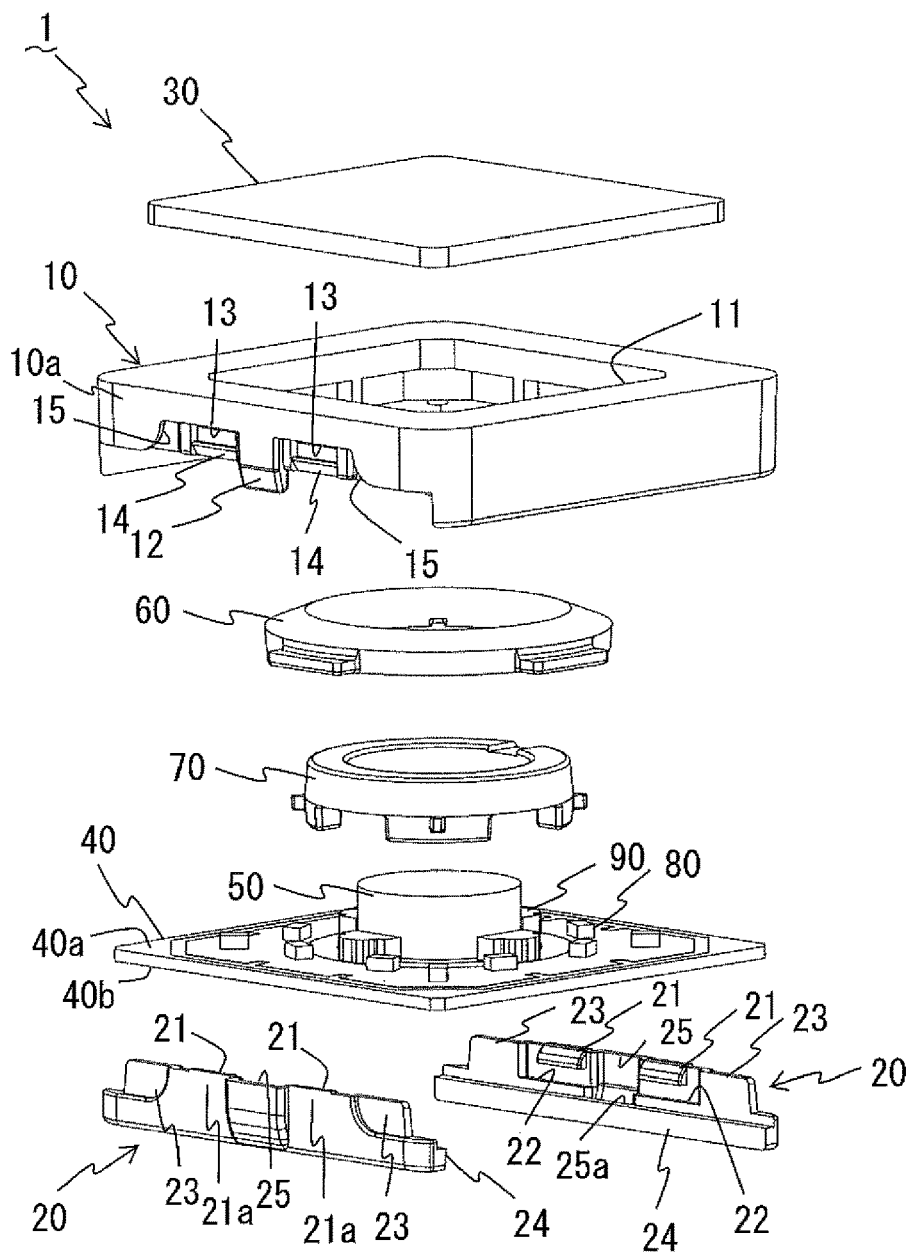
FIG. 2 is a top side exploded perspective view illustrating the imaging apparatus according to the embodiment.

FIG. 1 is a top side perspective view illustrating the imaging apparatus 1 according to the embodiment. FIG. 2 is a top side exploded perspective view illustrating the imaging apparatus 1 according to the embodiment.

Figure 3:
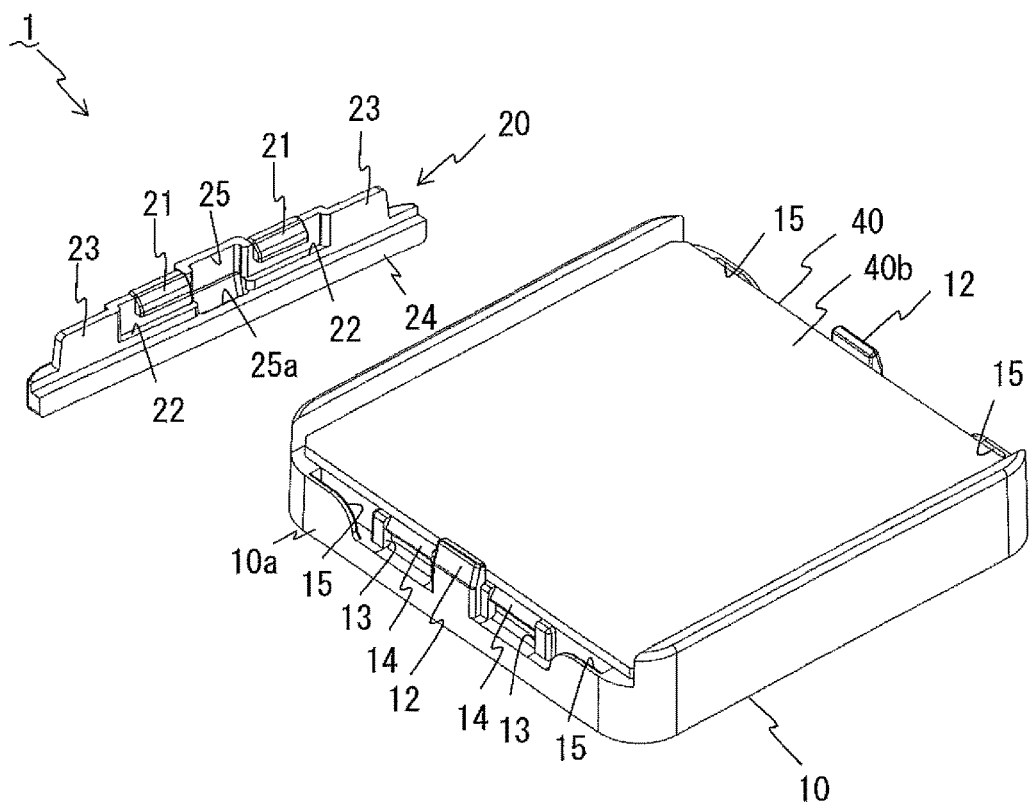
FIG. 3 is a bottom side perspective view illustrating the imaging apparatus, from which a stopper is removed, according to the embodiment.

FIG. 3 is a bottom side perspective view illustrating the imaging apparatus, from which a stopper 20 is removed, according to the embodiment.

Figure 5:
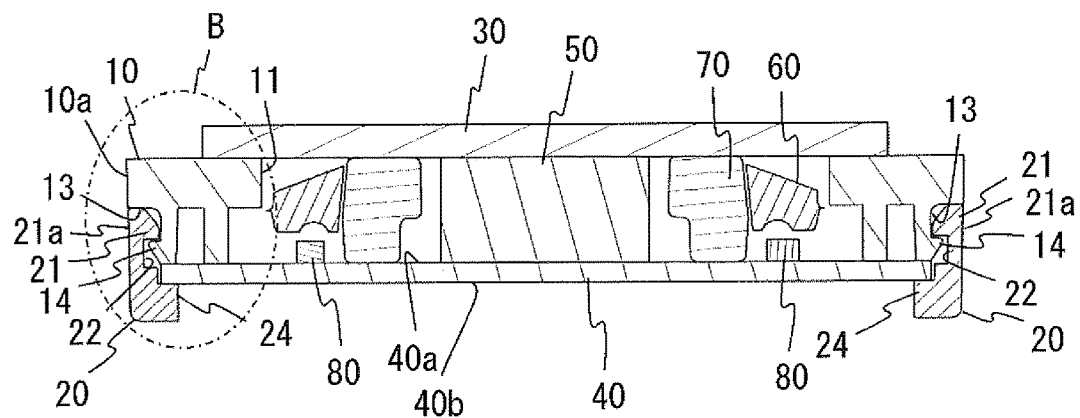
FIG. 5 is a V-V cross-sectional view of FIG. 1.
Figure 6:
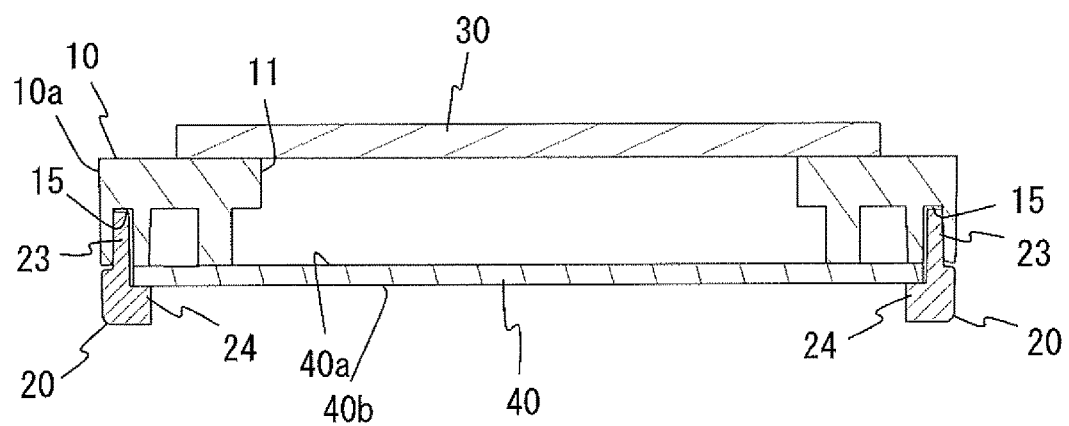
FIG. 6 is a VI-VI cross-sectional view of FIG. 1.

FIG. 4 is IV-IV cross-sectional view of FIG. 1. FIG. 5 is a V-V cross-sectional view of FIG. 1. FIG. 6 is a VI-VI cross-sectional view of FIG. 1.

Figure 8:
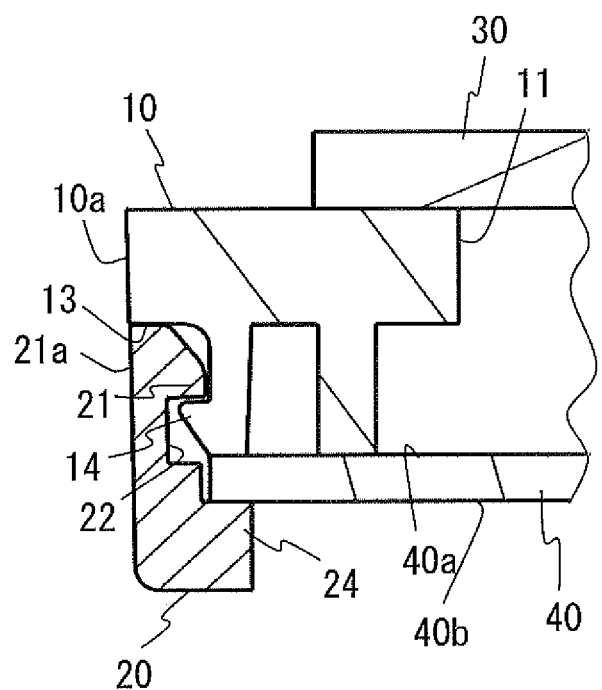
FIG. 8 is an enlarged view of a part B of FIG. 5.

FIG. 7 is an enlarged view of a part A of FIG. 4. FIG. 8 is an enlarged view of a part B of FIG. 5.

As illustrated in FIG. 2, the imaging apparatus 1 includes a housing 10, two stoppers 20, a top cover 30, a wiring substrate 40, an imaging unit 50, a light guide 60, a light shield ring 70, a plurality of light-emitting elements 80, and a plurality of photodetectors 90.

For example, the imaging apparatus 1 can be used as a biometric authentication apparatus that images biological information such as veins of the palm or the like, or an imaging apparatus for biometric authentication, which is part of the biometric authentication apparatus.

As illustrated in FIGS. 2 and 3, for example, the housing 10 takes the shape of a square frame in a planar view.

The housing 10 has a top opening part 11, a protruding part 12, stopper claw part housing parts 13, housing claw parts 14, and insertion part housing parts 15. As for the number of components of the housing 10, for example, one protruding part 12 is arranged for each of the stoppers 20, and two stopper claw part housing parts 13, two housing claw parts 14 and two insertion part housing parts 15 are arranged for each of the stoppers 20.

The top opening part 11 is open in the shape of a square that is smaller than the top cover 30 on the top surface of the housing 10. The bottom surface of the housing 10 is open wider than the top opening part 11.

As illustrated in FIGS. 4 and 7, the protruding part 12 protrudes from a back surface 40b of the wiring substrate 40. The back surface 40b of the wiring substrate 40 is a surface on a side opposite to a front surface 40a, on which an imaging element is mounted, on the side of the imaging unit 50 in the wiring substrate 40. Also, bottom edges of two surfaces on which the stopper 20 is not arranged from among the four surfaces of front, back, right and left, which are an outer peripheral surface 10a of the housing 10, protrude from the back surface 40b of the wiring substrate 40. For example, the protruding part 12 is provided at the center on the four sides of the housing 10 in planar view.

As illustrated in FIGS. 5 and 8, the stopper claw part housing parts 13 house an engagement portion of the entirety (the engagement portion of the stopper claw part 21 with the housing claw part 14, and a portion positioned on the side of the outer peripheral surface 21a in the engagement portion) of the stopper claw part 21. The stopper claw part housing parts are one example of the engagement part housing part. Moreover, the stopper claw parts 21 are one example of the engagement part. The stopper claw parts 21 and the housing claw parts 14 will be described in detail later.

The housing claw parts 14 protrude on the side of the outer peripheral surface 10a, and respectively engage with the stopper claw parts 21. The housing claw parts 14 are inserted into housing claw part concave parts 22. The housing claw parts 14 are positioned further inward than the outer peripheral surface 10a, and do not protrude from the outer peripheral surface 10a.

As illustrated in FIG. 6, the insertion part housing parts 15 are open on the side of the bottom surface of the housing 10, and insertion parts 23 are respectively inserted from below.

As illustrated in FIG. 2, each of the stoppers 20 includes stopper claw parts 21, housing claw part concave parts 22, insertion parts 23, a substrate pressing part 24, and a protruding part concave part 25. For example, two stopper claw parts 21, two housing claw part concave parts 22, and two insertion parts 23 are provided. The stoppers 20 fix the wiring substrate 40 to the housing 10 by sandwiching the wiring substrate 40 between the housing 10 and the stoppers 20.

The stoppers 20 are respectively arranged on two mutually facing surfaces from among the four front, back, right and left surfaces, which are the outer peripheral surface 10a of the housing 10, namely, two mutually facing sides of the wiring substrate 40. The stoppers 20 configure part of the bottom side of the outer peripheral surface of the imaging apparatus 1. Thus, the outer peripheral surface 10a of the housing 10 and that of the stoppers 20 configure the outer peripheral surface of the imaging apparatus 1. The stoppers 20 are inserted from the bottom side of the housing 10. It is desirable to arrange two stoppers 20 so that they mutually face each other, as in this embodiment. Note that the number and the locations (sides on which the stoppers 20 are arranged) of the stoppers 20 are not limited.

As illustrated in FIGS. 5 and 8, the stopper claw parts 21 engage with the outer peripheral surface 10a (the housing claw parts 14 provided on the outer peripheral surface 10a) of the housing 10 by being inserted into the stopper claw part housing parts 13 formed on the outer peripheral surface 10a of the housing 10. The stopper claw parts 21 are one example of the engagement part. Moreover, the outer peripheral surface 21a of the stopper claw parts 21 is positioned on the same surface as the outer peripheral surface 10a of the housing 10. The configuration of the engagement part does not always need to be a configuration where the engagement part is hooked by the claw parts. For example, the configuration of the engagement part may be another configuration where the engagement part engages with the outer peripheral surface of the housing 10.

The housing claw part concave parts 22 are open on the side of the inner peripheral surface of the stopper 20, namely, on the inner side of the imaging apparatus 1, and the housing claw parts 14 are inserted as described above.

The insertion parts 23 are provided on the sides of both ends that interpose the two housing claw part concave parts 22. Each of the insertion parts 23 takes, for example, the shape of a plate, and is inserted into the insertion part housing part 15 from below, as described above.

Each of the substrate pressing parts 24 is located at a position where the wiring substrate 40 is pressed, and sandwiches the wiring substrate 40 between the housing 10 and the local substrate pressing part. For example, the substrate pressing part 24 is provided over the entire length in the long-side direction of the stopper 20, and presses the rim of the back surface 40b of the wiring substrate 40 over the entire length of one side of the wiring substrate 40.

Similarly to the housing claw part concave parts 22, the protruding part concave part 25 is open on the side of the inner surface of the stopper 20, namely, on the inner side of the imaging apparatus 1, and the above described protruding part 12 is inserted. Into a hook groove 25a, which is the bottom end of the protruding part concave part 25, a tip of the protruding part 12 is inserted. Thus, the substrate pressing part 24 is hooked onto an inner peripheral surface 12a, illustrated in FIG. 7, of the protruding part 12. Thus, for example, the hook groove 25a functions as a hook part. Note that the hook groove 25a is arranged between the two stopper claw parts 21 in a planar view.

The top cover 30 takes, for example, the shape of a square, and is arranged on the top opening part 11 of the housing 10. The top cover 30 is formed with a translucent material since illumination light irradiated onto a target object to be imaged (such as veins of the palm) and light reflected from the target object to be imaged pass through.

The wiring substrate 40 is arranged on the bottom side of the imaging apparatus 1. Components such as a CPU, a memory and the like are mounted, so that the wiring substrate 40 functions as a control unit for imaging. Moreover, when the imaging apparatus 1 is used as a biometric authentication apparatus, the wiring substrate 40 can function as a control unit for biometric authentication.

The imaging unit 50 includes a lens module (not illustrated) and an imaging element (not illustrated) mounted on the wiring substrate 140. The imaging unit 50 is housed within the housing 10.

The light guide 60 takes, for example, the shape of a circle, and guides light emitted from the light-emitting element 80, which will be described later, to a target object to be imaged via the top cover 30.

The light shield ring 70 is arranged between the imaging unit 50 and the light guide 60, and blocks light from being incident from the outer peripheral surface to the imaging unit 50.

The light-emitting element 80 is, for example, an LED, and a plurality of light-emitting elements 80 are mounted on the wiring substrate 40. Light emitted from the light-emitting element 80 is irradiated onto the target object to be imaged through the light guide 60 and the top cover 30 as described above.

For example, four photodetectors 90 are mounted on the wiring substrate 40 in the periphery of the imaging unit 50. The photodetectors 90 are arranged, for example, to control the quantity of light of the light-emitting element 80.

In the above described imaging apparatus 1, each of the protruding parts 12 is inserted into the hook groove 25a as illustrated in FIGS. 4 and 7. Accordingly, even though a load is applied to the top cover 30 downward and the force is applied to the substrate pressing part 24 via the wiring substrate 40, the stopper 20 does not move in a direction (see the arrow indicated by an X) where the substrate pressing part 24 separates from the wiring substrate 40 by using the stopper claw part 21 as a pivot point due to such an operation that the substrate pressing part 24 touches the inner peripheral surface 12a of the protruding part 12. Therefore, each of the stoppers 20 does not deviate from the position at which the stopper sandwiches the wiring substrate 40 between the housing 10 and the local stopper 20, whereby the stoppers 20 can securely fix the wiring substrate 40.

In the above described embodiment, the housing 10 includes the protruding parts 12 that protrude from the back surface 40b on the side opposite to the front surface 40a on the side of the imaging unit in the wiring substrate 40. Moreover, the stoppers 20 respectively include the stopper claw parts (engagement parts) 21, each of which engages with the outer peripheral surface 10a (the stopper claw part housing part 13 provided on the outer peripheral surface 10a) of the housing 10, and the hook grooves 25a (hook part), which are each hooked onto the inner peripheral surface 12a of the protruding part 12 of the housing 10.

Accordingly, the stopper 20 can prevent the substrate pressing part 24 from moving in a direction where the substrate pressing part 24 separates from the wiring substrate 40 by using the stopper claw part 21 as a pivot point due to an operation such that the substrate pressing part 24 touches the inner peripheral surface 12a of the protruding part 12. Moreover, the wiring substrate 40 can be fixed with a simple configuration using the stopper 20.

Therefore, according to this embodiment, the wiring substrate 40 can be securely fixed with a simple configuration using the stopper 20.

Additionally, in this embodiment, the tip of the protruding part 12 is inserted into the hook groove 25a, which is one example of the hook part. Accordingly, the wiring substrate 40 can be fixed with a simpler configuration.

Furthermore, in this embodiment, the housing 10 has the stopper claw part housing parts (engagement part housing parts) 13 that house the stopper claw parts (engagement parts) 21, and the outer peripheral surface 21a of the stopper claw part 21 and the outer peripheral surface 10a of the housing 10 are positioned on the same plane. Accordingly, the stopper claw parts 21 do not protrude from the outer peripheral surface 10a of the housing 10, whereby the wiring substrate 40 can be fixed with a simpler configuration.

Still further, in this embodiment, one example of the engagement part is the stopper claw part 21, and the housing 10 has the housing claw parts 14, each of which engages with the stopper claw part 21. Accordingly, the wiring substrate 40 can be more securely fixed. Moreover, a force applied to the hook part is distributed to the stopper claw part 21 and the housing claw part 14, and the hooks are provided in both of the stoppers 20 and the housing 10, whereby an area where the hook parts are hooked can be reduced. As a result, the housing 10 and the stoppers 20 can be prevented from being increased in size in the direction of an outer diameter of the housing 10. Accordingly, the wiring substrate 40 can be fixed with a simpler configuration.

Still further, in this embodiment, the stoppers 20 respectively have the plurality of stopper claw parts 21. Therefore, the stoppers 20 can fix the wiring substrate 40 more securely. Moreover, a force applied to the hook part is distributed to the plurality of stopper claw parts 21, whereby the area where the hook parts are hooked can be reduced. As a result, the housing 10 and the stopper 20 can be prevented from being increased in size in the direction of the outer diameter of the housing 10. Therefore, the wiring substrate 40 can be fixed more securely with a simpler configuration.

Still further, in this embodiment, each of the stoppers 20 is arranged on the two mutually facing sides of the wiring substrate 40. Accordingly, the wiring substrate 40 can be securely fixed with a simple configuration.

The invention claimed is:
1. An imaging apparatus, comprising:
an imaging unit;
a housing that houses the imaging unit;
a wiring substrate; and
a stopper that sandwiches the wiring substrate between the housing and the stopper, wherein
the housing has a protruding part that protrudes from a back surface of the wiring substrate on a side opposite to a front surface of the wiring substrate, the front surface facing a side of the imaging unit, and
the stopper has an engagement part that engages with an outer peripheral surface of the housing, a hook part that is hooked onto an inner peripheral surface of the protruding part of the housing, and a substrate pressing part that extends over an entire length of the stopper in a long side direction of the stopper, presses a rim of the back surface of the wiring substrate over an entire length of one side of the wiring substrate, and touches the inner peripheral surface of the protruding part.

2. The imaging apparatus according to claim 1, wherein the hook part has a hook groove into which a tip of the protruding part is inserted.

3. The imaging apparatus according to claim 1, wherein the housing further comprises an engagement part housing part that houses the engagement part, and
an outer peripheral surface of the engagement part and the outer peripheral surface of the housing are positioned on the same plane.

4. The imaging apparatus according to claim 1, wherein the engagement part of the stopper has a stopper claw part, and
the housing has a housing claw part that engages with the stopper claw part.

5. The imaging apparatus according to claim 1, wherein the stopper has a plurality of engagement parts.

6. The imaging apparatus according to claim 1, wherein the stopper is arranged on each of two mutually facing sides of the wiring substrate.

* * * * *